US007390881B2

(12) United States Patent
Petrik

(10) Patent No.: US 7,390,881 B2
(45) Date of Patent: Jun. 24, 2008

(54) RECOMBINANT THERAPEUTIC FUSION PROTEINS

(75) Inventor: Juraj Petrik, Peebles (GB)

(73) Assignee: Troyanys Limited, Peebles (GB)

( * ) Notice: Subject to any disclaimer, the term of this patent is extended or adjusted under 35 U.S.C. 154(b) by 2 days.

(21) Appl. No.: 11/124,971

(22) Filed: May 9, 2005

(65) Prior Publication Data

US 2005/0260220 A1 Nov. 24, 2005

Related U.S. Application Data

(63) Continuation of application No. 10/129,031, filed as application No. PCT/GB00/04191 on Nov. 1, 2000, now abandoned.

(30) Foreign Application Priority Data

Nov. 2, 1999 (GB) ................................. 9925966.5

(51) Int. Cl.
*C07K 1/00* (2006.01)
*C07H 21/00* (2006.01)
(52) U.S. Cl. ...................................... 530/350; 536/22.1
(58) Field of Classification Search ........................ None
See application file for complete search history.

(56) References Cited

FOREIGN PATENT DOCUMENTS

| WO | WO 98/40492 | 9/1998 |
|---|---|---|
| WO | WO 99/64073 | 12/1999 |
| WO | WO 00/55207 | 9/2000 |

OTHER PUBLICATIONS

Hammond, Anthea L., et al. "Single-Chain Antibody Displayed on a Recombinant Measles Virus Confers Entry through the Tumor-Associated Carcinoembryonic Antigen." *Journal of Virology* 75(5):2087-2096 (Mar. 2001).
Lecouturier, V. et al. "Identification of Two Amino Acids in Hemagglutinin Glycoprotein of Measles Virus (MV) That Govern Hemadsorption, Hel. a Cell lusion. and CD46 Downregulation: Phenotypic Markers That Differentiate Vaccine and Wild-Type MV Strains" *Journal of Virology* 70: pp. 4200-4204, (1996).
Bende et al. Update: Search for an AIDS vaccine. AIDS Read, 10(9), 2000, pp. 526-537.
Beyrer. The HIV/AIDS vaccine research effort: An update. The Johns Hopkins University AIDS Service, The Hopkins HIV Report, Vol. 15(1), Jan. 2003, pp. 1-16.
Desrosiers. Prospects for an AIDS vaccine. Nature Medicine, vol. 10(3), Mar. 2004, pp. 221-223.
Feinberg et al. AIDS vaccine models: challenging challenge viruses. Nature Medicine, vol. 8(3), Mar. 2002, pp. 207-210.
Klausner et al. The need for a global HIV vaccine enterprise. Science, vol. 300, Jun. 2003, pp. 2036-2039.
Lee. Chapter 32 AIDS Vaccines: 32.1 Acquired immunodeficiency disease vaccines: design and development. AIDS: Biology, Diagnosis, Treatment, and Prevention, fourth edition, edited by DeVitat, Jr. et al., Lippincott-Raven, 1997, pp. 605-616.
Nabel. Challenges and opportunities of development of an AIDS vaccine. Nature, vol. 410, Apr. 2001, pp. 1002-1007.
Woelk et al. Immune and artificial selection in the haemagglutinin (H) glycoprotein of measles virus. Journal of General Virology, 2001, 82, 2463-2474.
Hummel et al., "Localization of Monoclonal Antibody Epitopes and Functional Domains in the Hemagglutinin Protein of Measles Virus", *Journal of Virology* 69: 1913-1916 (1995).
Patterson et al., "Structural and Functional Studies of the Measels Virus Hemagglutinin: Identification of a Novel Site Required for CD46 Interaction", Virology 256: 142-151 (1999).

*Primary Examiner*—Bruce Campell
*Assistant Examiner*—Nicole Kinsey White
(74) *Attorney, Agent, or Firm*—Myers Bigel Sibley & Sajovec, P.A.

(57) ABSTRACT

A recombinant bifunctional fusion protein comprises a first component which is the antigenic ectodomain of measles virus hemagglutinin protein (MeaH) genetically modified not to bind to human cells; and a second component fused thereto which is capable of binding to the surface structure of genetically variable viruses such as HCV or HIV or other therapeutic targets. The second component binds to the target and the first component is recognised by anti-measles antibodies present in the majority of the population. The protein may be used therapeutically to treat HCV or HIV infection or against other therapeutic targets.

10 Claims, 2 Drawing Sheets

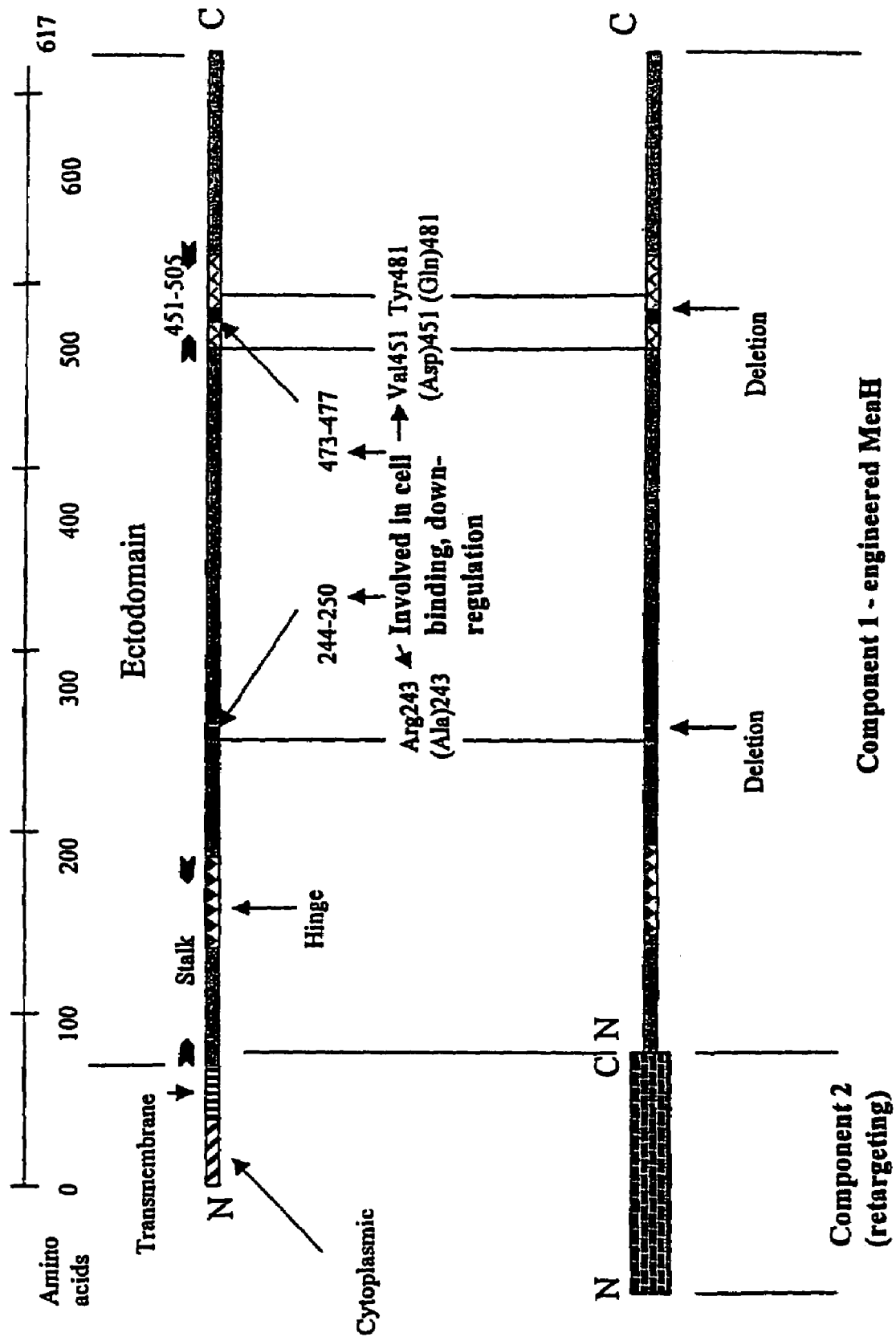

Fig.2: Western blot of HIV1 envelope (gp 120) - binding proteins from selected clones of expression cDNA library 1 - 11: Lysates from clones binding to HIV1 env, selected by high density screening;
N: Lysates from negative control clones
M: Molecular weight markers

```
                         SEQUENCE LISTING

<160> NUMBER OF SEQ ID NOS: 15

<210> SEQ ID NO 1
<211> LENGTH: 372
<212> TYPE: DNA
<213> ORGANISM: Homo sapiens

<400> SEQUENCE: 1
cacgcgtccg ctgaagaaga aattcaggaa atctgcttaa agatcttgca gctttatgct      60
cggaaaaagg ttgatctcac acacctggag ggtgaagtgg aaaaagaaag cacgctatcg     120
aagaggcaaa ggcccaagcc cggggcctgt tgcctggggg cacacaggtg ctggatggta     180
cctcggggtt ctctcctgcc cccaagctgg tggaatcccc caaagaaggt aaagggagca     240
agccttcccc actgtctgtg aagaacacca agaggaggct ggagggcgcc aagaaagcca     300
aggcggacag ccccgtgaac ggcttgccaa aggggcgaga gagtcggagt cggagccgga     360
gccgtgagca ga                                                         372

<210> SEQ ID NO 2
<211> LENGTH: 33
<212> TYPE: DNA
<213> ORGANISM: Measles virus

<400> SEQUENCE: 2
ggcctcgagt ctgcgattgg ttccatcttc ccg                                   33

<210> SEQ ID NO 3
<211> LENGTH: 33
<212> TYPE: DNA
<213> ORGANISM: Measles virus

<400> SEQUENCE: 3
cgcggatcca tgtcaccaca acgagaccgg ata                                   33

<210> SEQ ID NO 4
<211> LENGTH: 33
<212> TYPE: DNA
<213> ORGANISM: Measles virus

<400> SEQUENCE: 4
cgcggatccc ttcatcgggc agccatctac acc                                   33

<210> SEQ ID NO 5
<211> LENGTH: 28
<212> TYPE: DNA
<213> ORGANISM: Artificial sequence
<220> FEATURE:
<223> OTHER INFORMATION: Synthetic oligonucleotide primer
<220> FEATURE:
<221> NAME/KEY: misc_feature
```

```
<223> OTHER INFORMATION: Sense primer used for mutagenesis of
      Arg243 -> Ala

<400> SEQUENCE: 5
ctgagcagca aagcgtcaga gttgtcac                                             28

<210> SEQ ID NO 6
<211> LENGTH: 28
<212> TYPE: DNA
<213> ORGANISM: Artificial sequence
<220> FEATURE:
<223> OTHER INFORMATION: Synthetic oligonucleotide primer
<220> FEATURE:
<221> NAME/KEY: misc_feature
<223> OTHER INFORMATION: Antisense primer used for mutagenesis of
      Arg243 -> Ala

<400> SEQUENCE: 6
gtgacaactc tgacgctttg ctgctcag                                             28

<210> SEQ ID NO 7
<211> LENGTH: 32
<212> TYPE: DNA
<213> ORGANISM: Artificial sequence
<220> FEATURE:
<223> OTHER INFORMATION: Synthetic oligonucleotide primer
<220> FEATURE:
<221> NAME/KEY: misc_feature
<223> OTHER INFORMATION: Sense primer used for mutagenesis of
      Val451 -> Asp

<400> SEQUENCE: 7
ccaaccacaa caatgactat tggctgacta tc                                        32

<210> SEQ ID NO 8
<211> LENGTH: 32
<212> TYPE: DNA
<213> ORGANISM: Artificial sequence
<220> FEATURE:
<223> OTHER INFORMATION: Synthetic oligonucleotide primer
<220> FEATURE:
<221> NAME/KEY: misc_feature
<223> OTHER INFORMATION: Antisense primer used for mutagenesis of
      Val451 -> Asp

<400> SEQUENCE: 8
gatagtcagc caatagtcat tgttgtggtt gg                                        32

<210> SEQ ID NO 9
<211> LENGTH: 30
<212> TYPE: DNA
<213> ORGANISM: Artificial sequence
<220> FEATURE:
<223> OTHER INFORMATION: Synthetic oligonucleotide primer
<220> FEATURE:
<221> NAME/KEY: misc_feature
<223> OTHER INFORMATION: Sense primer used for mutagenesis of
      Tyr481 -> Gln

<400> SEQUENCE: 9
caaggttagt ccccagctct tcaatgtccc                                           30

<210> SEQ ID NO 10
<211> LENGTH: 30
<212> TYPE: DNA
<213> ORGANISM: Artificial sequence
<220> FEATURE:
<223> OTHER INFORMATION: Synthetic oligonucleotide primer
<220> FEATURE:
```

<221> NAME/KEY: misc_feature
<223> OTHER INFORMATION: Antisense primer used for mutagenesis of
     Tyr481 -> Gln

<400> SEQUENCE: 10
gggacattga agagctgggg actaaccttg                                        30

<210> SEQ ID NO 11
<211> LENGTH: 38
<212> TYPE: DNA
<213> ORGANISM: Artificial sequence
<220> FEATURE:
<223> OTHER INFORMATION: Synthetic oligonucleotide primer
<220> FEATURE:
<221> NAME/KEY: misc_feature
<223> OTHER INFORMATION: Sense primer used for deletion of Leu247 and
     Ser248

<400> SEQUENCE: 11
gagcagcaaa aggtcagagc aactgagcat gtaccgag                               38

<210> SEQ ID NO 12
<211> LENGTH: 38
<212> TYPE: DNA
<213> ORGANISM: Artificial sequence
<220> FEATURE:
<223> OTHER INFORMATION: Synthetic oligonucleotide primer
<220> FEATURE:
<221> NAME/KEY: misc_feature
<223> OTHER INFORMATION: Antisense primer used for deletion of Leu247
     and Ser248

<400> SEQUENCE: 12
ctcggtacat gctcagttgc tctgaccttt tgctgctc                               38

<210> SEQ ID NO 13
<211> LENGTH: 32
<212> TYPE: DNA
<213> ORGANISM: Artificial sequence
<220> FEATURE:
<223> OTHER INFORMATION: Synthetic oligonucleotide primer
<220> FEATURE:
<221> NAME/KEY: misc_feature
<223> OTHER INFORMATION: Sense primer used for deletion of Arg475

<400> SEQUENCE: 13
cattggagtg gataccgttc aaggttagtc cc                                     32

<210> SEQ ID NO 14
<211> LENGTH: 32
<212> TYPE: DNA
<213> ORGANISM: Artificial sequence
<220> FEATURE:
<223> OTHER INFORMATION: Synthetic oligonucleotide primer
<220> FEATURE:
<221> NAME/KEY: misc_feature
<223> OTHER INFORMATION: Antisense primer used for deletion of Arg475

<400> SEQUENCE: 14
gggactaacc ttgaacggta tccactccaa tg                                     32

<210> SEQ ID NO 15
<211> LENGTH: 436
<212> TYPE: DNA
<213> ORGANISM: Homo sapiens

<400> SEQUENCE: 15
ggagaaggtc tctgaaggag aaaagcaaag aagctctttt ggcctcacaa aagccattta       60

```
aatttatagc aagggaggaa cagaagcgag cagcccggga aaagcagctg agagactttc    120
ttaagtataa aaagaaaaca aatcgattta aagccagacc cattcctcga tctacttatg    180
gttcaactac caatgacaag ttaaaagaag aagagctcta tcgaaacctt aggacacagc    240
tgagagccca ggagcattta cagaactcat ctcctctgcc ttgtaggtca gcttgcggat    300
gcaggaaccc caggtgtcct gaacaggctg taaagttgaa gtgtaaacac aaggttaggt    360
gcccactcct gattttgagg accttctgag agataccaga accctctcaa acacaagtct    420
tcaaaactct aacagg                                                    436
```

RECOMBINANT THERAPEUTIC FUSION PROTEINS

STATEMENT OF PRIORITY

The present application is a continuation of, and claims priority to, U.S. application Ser. No. 10/129,031, filed Oct. 1, 2002 now abandoned, which is a 35 U.S.C. §371 national phase application of International Application Serial No. PCT/GB00/04191, filed Nov. 1, 2000 and published in English as PCT Publication No. WO 01/32893 A1 on May 10, 2001, which claims priority to Great Britain Patent Application No. GB 9925966.5, filed Nov. 2, 1999, the disclosure of each of which is incorporated herein by reference in its entirety.

FIELD OF THE INVENTION

This invention relates to novel bifunctional recombinant fusion proteins, particularly though not exclusively for treating infections with genetically variable viruses and other therapeutic targets against which it is difficult to develop vaccines.

BACKGROUND OF THE INVENTION

The principle of vaccination has been known since the 18th century in the form of empirical treatment against smallpox. The first scientific vaccine was developed by Pasteur (rabies). This was a first generation vaccine, as was the smallpox vaccine, using live animals for production. Second generation vaccines are produced in eggs (Influenza, Yellow fever) and third generation vaccines are produced in cell culture (Polio, Measles, Rubella, Mumps, Tickborne encephalitis). Fourth generation vaccines are produced in various expression systems by recombinant DNA technology and are represented by hepatitis B virus surface antigen (HBsAg).

A vaccine can consist of the whole microorganism (bacteria, virus, parasite etc.) or its part (subunit vaccine). In the former case the microorganism is either inactivated (killed) or attenuated. In addition, as mentioned above, recombinant antigens or synthetic immunogenic peptides have been used recently and DNA vaccines have been developed relying on the host cell to produce the desired antigen(s).

The primary purpose of vaccination is and always has been prophylactic—prevention of particular disease.

Nevertheless, even relatively speedy development of vaccines against some life-threatening diseases may be too late for people already infected. The number of people infected worldwide with three of the most common human viruses—hepatitis B virus (HBV), hepatitis C virus (HCV) and human immunodeficiency virus (HIV) represents up to 10% of human population when the latest figures of 300-400 million for HBV, more than 60 million for HCV and more than 30 million for HIV are combined. There is thus a clear need for therapeutics and one of the options is development of therapeutic vaccines.

Vaccine development is expensive and the cost of developing a vaccine is between $US 50 million and 200 million. Much of the cost reflects efforts to make sure that a variety of antigenic variants of the particular infectious agent are disarmed by the vaccine. This is difficult with moderately genetically divergent microorganisms but it is almost impossible with viruses having antigens as variable as the surface glycoproteins of HIV, HCV or influenza. On the other hand, there are highly successful vaccines with a proven record of efficacy and safety, such as polio and measles, mumps and rubella (MMR). The main difference between HCV, HIV and influenza on the one hand and polio, measles, mumps and rubella on the other hand is that members of the latter group against which there are successful vaccines are genetically much more stable than the former group.

Influenza vaccination is targeted each season at particular variants which are predicted to appear based on epidemiological studies. Experimental HIV vaccines are based on various constructs of envelope protein(s) originating from one or several strains. However, it is still unlikely that this approach will be effective for the entire spectrum or at least a majority of worldwide field isolates. There is no vaccine in trials for HCV yet.

In contrast, as mentioned earlier viruses such as measles are genetically more stable. Vaccine strains induce broadly cross-reactive antibodies. Measles hemagglutinin (MeaH) is a major target of these antibodies. It is a glycoprotein as is the second surface protein—fusion protein (F). Both of them are required for a fusion of cell membranes, but the sequence of events starts with MeaH binding to the cell receptor, thought to be CD46. MeaH is a membrane anchored protein with amino acids 1 to 34 proposed to form a cytoplasmic domain, while 35 to 58 comprise a transmembrane domain (see FIG. 1). Residues 59 to 181 are thought to form a stalk, part of which (135 to 181) probably forms a hinge of a molecule [Sato et al., J. Virol. 69, 513-516 (1995)1. Spikes of MeaH on virion surface consist of tetramers (dimers of disulfide bridge-linked homodimers). Cysteines 139 and 154 were suggested to participate in intermolecular disulfide bonding between monomeric MeaH glycoproteins. Soluble forms resulting from endoproteinase digestion of measles virus particles all reacted with monoclonal antibodies suggesting the preservation of antigenicity/reactivity [Sato et al., J. Virol. 69, 513-516 (1995)]. MeaH domain required for hemadsorption and hemagglutination activities was mapped between residues 451 and 505 [Hummel & Bellini, J. Virol. 69, 1913-1916 (1995)]. In addition to hemadsorption, the mutagenesis Val451Glu and Tyr481Asn also abrogated CD46 downregulation and HeLa cell fusion [Lecouturier et al., J. Virol. 70, 4200-4204 (1996)]. A novel site required for CD46 interaction was mapped between 473 and 477 [Patterson et al., Virology 256, 142-151 (1999)]. Additional neutralizing epitope NE244-250, located next to CD46 downregulating amino acid Arg 243, may be involved in CD46 binding [Fournier et al., J. Gen. Virol. 78, 1295-1302 (1997)].

It is an object of the present invention to provide a therapy for people infected with genetically variable viruses and other therapeutic targets.

BRIEF DESCRIPTION OF THE DRAWINGS

FIG. 1 depicts the normal and engineered forms of hemagglutinin of the Measles virus (vaccine strain).

FIG. 2 depicts a Western blot of HIV1 envelope (gp 120)-binding proteins from selected clones of an expression cDNA library.

SUMMARY OF THE INVENTION

The present invention provides a recombinant bifunctional fusion protein which comprises:
- a first component which is a measles virus protein modified so that it does not bind to CD46 receptor or cause hemadsorption or hemagglutination, but retains its antigenicity and is recognised by anti-measles antibodies; and
- a second component fused to the first component and which is capable of binding to genetically variable viruses or other therapeutic targets.

The present invention is based on the use of a component (the "second component") which recognises and binds specifically to the target. Any such binding entity is suitable, and is particularly one which is capable of binding to conserved peptide sequences in the surface structure of the variable virus, such as envelope glycoproteins. Neutralising antibodies required for successful vaccine formulations are generally directed against variable surface proteins. The present invention avoids the problem of variability by employing an entity which, whilst not neutralising the virus, is able to bind to surface proteins which are conserved between viral strains.

Viral clearance is achieved by fusing the first component thereto. This first component is recognised by anti-measles antibodies present in the general population as a result of mass vaccination programs. Preferably, the first component is the ectodomain of measles virus hemagglutinin protein (MeaH). The MeaH first component does not cause viral disease in itself but retains its antigenicity and is recognised and bound by prevalent anti-measles antibodies. This enables the fusion protein of the present invention to be therapeutically useful for the treatment of long term viral infection by variable viruses such as HCV and HIV.

Thus, a preferred embodiment of the invention provides bifunctional fusion proteins, one part of which is the ectodomain of measles virus hemagglutinin (MeaH) modified so that it does not bind to CD46 receptor or cause hemadsorption or hemagglutination, but retains its antigenicity and can be recognised by patients' anti MeaH antibodies and memory cells resulting from previous infection or vaccination. The second part of the fusion protein composition consists of a molecule or part of it capable of binding to the surface structure of HIV and HCV viruses, such as formed by their envelope glycoproteins.

These bifunctional proteins are capable of boosting the existing anti-measles immunity in a patient and at the same retargeting it against a new target, such as HIV or HCV virus, and are used as therapeutic vaccines to treat patients infected with agents against which the new composition is targeted.

A further aspect of the invention relates to polynucleotides (particularly DNA) coding for the recombinant fusion protein. These may be used as "DNA vaccines" for therapeutic antiviral purposes.

The invention also relates to pharmaceutical compositions comprising the fusion protein or polynucleotide, together with a pharmaceutically acceptable carrier. The carrier is generally an apyrogenic injection or infusion vehicle, such as saline solution; or may be an oral composition formulated in known manner for release in the gastrointestinal tract.

Embodiments of the invention will now be described by way of example only.

DESCRIPTION OF THE INVENTION

The present invention relates to a novel therapeutic approach using boost of the existing humoral and/or cellular immunity by the bifunctional fusion protein consisting of the antigen against which the treated individual has already developed antibodies, either as a result of previous infection or by vaccination, and the targeting part of the complex which mediates binding of the complex to the actual target. For the purpose of this embodiment the antigen is the hemagglutinin of the measles virus (MeaH), modified in several ways in order to suit optimally the proposed approach. The measles F protein may also be modified for use in the invention. Most functions of MeaH carried out in the normal replication cycle were eliminated for the purpose of the present invention. The requirements for MeaH as a booster/carrier antigen are as follows:

1) Preserved immunogenicity/reactivity with existing antibodies and preserved recognition by memory cells
2) Solubility/absence of membrane anchoring
3) Providing a linker/hinge between two unrelated parts of a new fusion molecule
4) Absence of CD46 binding
5) Absence of erythrocyte binding/agglutination For the purpose of introducing these changes, constructs of the MeaH gene of the Measles vaccine strain lacking between 58 and 100 N-terminal amino acids were amplified by PCR and cloned (FIG. 1). These clones were further modified by site directed mutagenesis of codons for amino acids 451 and 481, as well as 243. In addition, small deletions were introduced in the regions 244-250 and 450-505 (particularly 473-477). The selection criteria were: lack of binding to CD46, lack of hemadsorption and hemagglutination activities. At the same time the successful constructs retain their antigenicity/ability to be recognised by antibodies from vaccinated individuals.

As second component, several candidate molecules retargeting the complex to variable viral targets, namely hepatitis C virus (HCV) and human immunodeficiency virus (HIV) are presented. Other therapeutic targets include other pathogens; and surface structures, proteins and epitopes specific to cancerous cells. Prion proteins implicated in Creuzfeld Jakob disease (CJD) or new variant CJD (nvCJD) may also be targeted. In order to avoid unwanted immune reaction to this portion of the complex molecule, only retargeting proteins of human origin are considered for human therapy. Candidate molecules are single chain antibodies (scFv) which can be selected from large phage display libraries. Monoclonal antibodies may also be used. For HCV it is known that at least a subpopulation of the virus in the bloodstream is associated with low density lipoprotein (LDL) fraction, most probably through binding between the HCV E1 glycoprotein and apolipoprotein B (apoB) of LDL. ApoB has therefore been subjected to chemical fragmentation and relevant fragments binding to the HCV virion and/or HCV E1 glycoprotein were determined. These were fused at gene level with MeaH, modified as described above.

Similarly, candidate molecules or their parts for HIV binding were studied. For this purpose, expression libraries prepared from sources which mostly do not come into contact with the virus were investigated to discover previously unknown proteins capable of binding the accessible structures of the HIV virion. Several binding proteins were identified in a library from human brain and some of them sequenced. Two clones with relatively high binding activity were:

1) a clone with coding sequence for human creatine kinase B.
2) a clone for an unknown human protein, partial sequence of which reads as follows.

5'-CACGCGTCCGCTGAAGAAGAAATTCAGGAAATCTGCTTAAAGATCTT (SEQ ID NO:1)
GCAGCTTTATGCTCGGAAAAAGGTTGATCTCACACACCTGGAGGGTGA

```
                            -continued
AGTGGAAAAAGAAAGCACGCTATCGAAGAGGCAAAGGCCCAAGCCC
GGGGCCTGTTGCCTGGGGGCACACAGGTGCTGGATGGTACCTCGGG
GTTCTCTCCTGCCCCCAAGCTGGTGGAATCCCCCAAAGAAGGTAAAGG
GAGCAAGCCTTCCCCACTGTCTGTGAAGAACACCAAGAGGAGGCTGG
AGGGCGCCAAGAAAGCCAAGGCGGACAGCCCCGTGAACGGCTTGCC
AAAGGGGCGAGAGAGTCGGAGTCGGAGCCGGAGCCGTGAGCAGA-3'.
```

Variants of these clones differing by no more than 5% of amino acid positions and still binding to HIV envelope protein would also be suitable.

Using methods as described for apolipoprotein B above, the fragments of these proteins mediating binding to HIV virion and/or env protein, were fused with constructs of MeaH, modified as described earlier.

The principal idea of this invention is to use immunological memory existing within a majority of the population against a genetically stable antigen as a result of a natural infection or, preferably, vaccination (which has the added advantage of available records and standard methodology), and to redirect it towards infectious or other agents, against which it is difficult to prepare vaccines because of genetic variability or other reasons. Measles hemagglutinin (MeaH) has been chosen for several reasons:

1) Vaccination against measles has proven successful over a long period of time and measles is one of the future candidates for global eradication. Thus, there is a high vaccination coverage also in most developing countries.
2) Most of the protective activity against the measles virus (MV) has been shown to be directed against hemagglutinin.
3) There is sufficient structural and functional data available on the hemagglutinin.

This type of retargeting may be very widely applicable depending on the availability of binding/retargeting molecule or motif and may include apart from infectious agents also cancer cells. However, in the present invention the emphasis is on variable human viruses, namely HIV and HCV. Especially the HIV prevalence figures in some African and Asian regions are critical and swift novel therapeutic approaches are needed.

It is well known that patients with AIDS suffer from dysfunction of their immune system. Questions can therefore be asked what are the levels of antibodies against former vaccination antigens, such as Measles, and how is the immunological memory affected in these patients. Surprisingly, waning measles immunity was not greatly accelerated in HIV-infected adults despite progressive HIV-related immunodeficiency [Zolopa et al., Clinical Infectious Diseases 18, 636-638 (1994)]. Levels of measles antibody remained stable in both, HIV-infected progressors and non-progressors [Brostrom et al., Clinical and Experimental Immunology 106, 35-39(1996)] and 95% of 210 HIV-positive patients had Measles antibody regardless of the CD4 counts [Wallace et al., Vaccine 12, 1222-1224 (1994)].

HCV-infected individuals are not known to have their immune system affected in this way and no limitations of the therapeutic approach described are anticipated.

EXAMPLES

The following examples are provided for purposes of illustration only and are not to be viewed as a limitation of the scope of the invention. FIG. 1 attached hereto shows schematically the genetic engineering involved. FIG. 2 shows binding of proteins expressed by certain cDNA clones (useful as first component) to HIV envelope glycoprotein. In the following, μl means microlitres, ' means minute and " means seconds other than in nucleotide sequences.

Example 1

Amplification and Cloning of the Gene for Hemagglutinin of the Vaccine Strain of Measles Virus RNA was extracted from Edmonston strain of Measles virus using RNasol B (AMS Biotechnology) according to the manufacturer's instruction. RNA was washed with 80% ethanol twice, air-dried and dissolved in 100 μl of DEPC-treated water.

cDNA synthesis: 30 μl of RNA was mixed with 13 μl (25 pMol/μl) of primer XhoMH/full/A [5'-ggCCTCgAgTCTgC-gATTggTTCCATCTTCCCg-3' (SEQ ID NO:2); 33-mer], heated for 10 minutes at 70° C. and cooled on ice.

Following components of the reaction mix were added: 34.5 μl water/DEPC; 4 μl 25 mM mix of dATP, dCTP, dGTP, dTTP; 5 μl 10× Super Reverse Transcriptase (Super RT) (HT Biotechnology) buffer; 2.5 μl (100 U) RNasin (Promega Corporation) 4 μl Super RT. Reaction mix (final volume 100 μl) was incubated for 40 minutes at 42° C.

Resulting cDNA was used to amplify two variants of MeaH: full-length (MeaHfl) and short variant, lacking 59 N-terminal amino acids (MeaHsv). MeaHfl is designated for comparative purposes, MeaHsv is designated for further mutagenesis and fusion with retargeting part of the bifunctional molecules.

| MeaHfl | MeaHsv |
| --- | --- |
| 5 μl cDNA | 5 μl cDNA |
| 5 μl 10 × PCR buffer II | 5 μl 10 × PCR buffer II |
| 3 μl 25 mM MgCl$_2$ | 3 μl 25 mM MgCl$_2$ |
| 1.6 μl 2.5 mM dNTPs | 1.6 μl 2.5 mM dNTPs |
| 1.6 μl 25 pMol/μl primer BamMH/full/S* | 1.6 μl 25 pMol/μl primer BamMH/short/S** |
| 1.6 μl 25 pMol/μl primer XhoMF/full/A | 1.6 μl 25 pMol/μl primer XhoMF/full/A |
| 31.7 μl water/DEPC | 31.7 μl water/DEPC |
| 0.5 μl AmpliTaq | 0.5 μl AmpliTaq |

*BamMH/full/S: 5'-CgCggATCCATgTCACCACAACgAgACCggATA-3' (SEQ ID NO: 3)
**BamMH/short/S: 5'-CgCggATCCCTTCATCgggCAgCCATCTACACC-3' (SEQ ID NO: 4)

Reaction mixtures were overlaid with 50 μl of mineral oil. AmpliTaq was added during the first denaturation step (95° C.). PCR was done using Trioblock and the following programme:

```
1 cycle          95° C./3' and 65° C./30";
30 cycles        72° C./60"; 95° C./30"; 65° C./30";
final extension  72° C./7'.
```

2.5 μl aliquots of PCR reactions were analysed by agarose gel electrophoresis. PCR reaction products were cleaned according to manufacturer's instruction using QPCR purification spin column kit (Qiagen) and eluted into 50 µl of elution buffer.

Cloning into Vector TOPO 2.1 for Subcloning:

1 µl of TOPO 2.1 DNA provided in TA cloning kit (Invitrogen) was mixed with 1.5 µl of each PCR eluate and 2.5 µl water. During a 5 minute incubation at room temperature, 2 µl of beta-mercapto-ethanol was added to each aliquot of TOP 10 cells (Invitrogen). 1 µl of plasmid-insert mixture was added to TOP 10 cells, incubated on ice for 30 minutes, heat-shocked at 42° C. for 30 seconds and cooled on ice for two minutes. 250 µl of SOC medium (Invitrogen kit) was added to each transformation and tubes placed horizontally in a shaker at 37° C. for 30'. 10 and 100 µl were plated on agar plates with ampicillin (100 µg/ml) to which 40 µl of 40 mg/ml X-Gal was added some 30 minutes earlier.

5 white colonies of each construct were grown overnight in TYE medium containing 100 µg/ml ampicillin and plasmid DNA extracted using plasmid mini Prep (Qiagen). Presence of the inserts of correct size was checked after simultaneous digestion of plasmid DNAs with BamHI and XhoI. Restriction endonucleases and reaction components (buffer 2; BSA) were from New England Biolabs—NEB. Reactions were incubated 1 hour at 37° C. and 25 µl of each reaction run on the agarose gel and inserts cleaned by Qiaquick gel purification kit (Qiagen) according to the manufacturer's instruction.

Cloning into Plasmid cDNA4/HisMax A, B and C for Mutagenesis and Expression.

Three variants of pcDNA4/HisMax (A, B and C; Invitrogen) are used to ensure in-frame cloning of the inserts. The plasmid is designed for overproduction of recombinant proteins in mammalian cell lines.

DNAs of A, B and C variants of the plasmid were digested with BamHI and XhoI and gel-purified as described above for inserts. Purified plasmids and inserts were ligated together in standard ligation reaction and TOP 10 cell were transformed as described above.

White colonies were grown as described above and in-frame inserts checked by sequencing.

Example 2

In Vitro Mutagenesis of MeaHfl and MeaHsv.

Main targets for mutagenesis were:

1. Site-directed mutagenesis of codon for amino acid 243.
2. Site-directed mutagenesis of codon for amino acid 451.
3. Site-directed mutagenesis of codon for amino acid 481
4. Short deletions in the regions between amino acids 244-250.
5. Short deletions in the regions between amino acids 450-505 (i.e., 473-477).

Mutagenesis is carried out using QuickChange Site-Directed Mutagenesis Kit (Stratagene). The advantage is that plasmids with cloned sequences of interest are mutated directly, without the need for further subcloning. Two complementary primers are needed for each mutation, where mutated nucleotide(s) or insertion/deletion should be positioned in the middle of the primers. The procedure involves digestion of original (nonmutated) DNA strands with DpnI. Procedures were carried out as described in the instruction manual.

Examples of primers used for mutagenesis:

1 Arginine 243:
Sense (28-mer):
5'-CTgAgCAgCAAAgCgTCAgAgTTgTCAC-3' (SEQ ID NO:5)

Antisense (28-mer):
5'-gTgACAACTCTgACgCTTTgCTgCTCAg-3' (SEQ ID NO:6)

Arginine 243 is changed to Alanine in this case.

2 Valine 451:
Sense (32-mer):
5'-CCAACCACAACAATgACTATTggCTgACTATC-3' (SEQ ID NO:7)

Antisense (32-mer):
5'-gATAgTCAgCCAATAgTCATTgTTgTggTTgg-3' (SEQ ID NO:8)

Valine 451 was changed to Aspartic acid in this case.

3 Tyrosine 481:
Sense (30-mer):
5'-CAAggTTAgTCCCCAgCTCTTCAATgTCCC-3' (SEQ ID NO:9)

Antisense (30-mer):
5'-gggACATTgAAgAgCTggggACTAACCTTg-3' (SEQ ID NO:10)

Tyrosine 481 was changed to Glutamine in this case.

4 Region 244-250: 6 nucleotide (2 amino acid) deletion of codons for Leu247-Ser248

Sense (38-mer):
5'-gAgCAgCAAAAggTCAgAgCAACTgAgCATgTACCgAg-3' (SEQ ID NO:11)

Antisense (38-mer):
5'-CTCggTACATgCTCAgTTgCTCTgACCTTTTgCTgCTC-3' (SEQ ID NO:12)

5 Region 451-505: 3 nucleotide (1 amino acid) deletion of codon for Arg475

Sense (32-mer):
5'-CATTggAgTggATACCgTTCAAggTTAgTCCC-3' (SEQ ID NO:13)

Antisense (32-mer):
5'-gggACTAACCTTgAACggTATCCACTCCAATg-3'    (SEQ ID NO:14)

In all 5 cases the example of the reaction was as follows (components of the system from the kit):
 5 µl of 10× reaction buffer
 5-50 ng of dS DNA template (starting with pcDNA4/His-Max/MeaHfl or pcDNA4/HisMax/MeaHsv)
 125 ng of primer 1
 125 ng of primer 2 (complementary)
 1 µl of dNTP mix
 ddH$_2$O to 50 µl
 1 µl (2.5 U) of PfuDNA polymerase Cycling Parameters:
 1 cycle 95° C. for 30"
 12 cycles (for point mutation)
 16 cycles (for single amino acid change) 95° C./30"; 55° C./1'; 68° C./14'
 18 cycles (for multiple amino acid deletions or insertions) (2' per kb of plasmid)
 After cycling the reactions were chilled on ice for 2'.

1 µl of µl DpnI (10 U) was added, reaction mixture was mixed, spun down shortly in microcentrifuge and incubated at 37° C. for 1 hour (removal of nonmutated DNA).

1 µl of each resulting mutated plasmid DNA was transformed into Epicurian Coli XL1-Blue supercompetent cells using standard procedure, as described in Example 1, except that the heat shock at 42° C. was for 45" when using Falcon 2059 polypropylene tubes. NZY+ broth (0.5 ml) was used to incubate transformation reaction at 37° C. for 1 hour with shaking at 225-250 rpm and spread on LB-ampicillin plates to which 20 µl of 10% (w/v) X-gal and 20 µl of 100 mM IPTG were added in advance. Colonies appear after 16 hours at 37° C.

pcDNA4/HisMax/MeaHfl and pcDNA4/hisMax/MeaHsv were mutagenised in parallel for comparative purposes, in stepwise manner: the product of mutagenesis reaction 1 (Arg 243 change) was used as template for the mutagenesis step 2 (Valine 451 change) after confirmation of mutated site by sequencing. Thus the final products of the site-directed mutagenesis contain all 5 types of mutations: Arg243; Val451; Tyr481; short deletions in region 244-250 and 473-477.

Variants of Measles hemagglutinin expressed by these mutagenised plasmids are investigated for loss of hemadsorption and cell receptor binding. Importantly, they should retain the ability to be recognised by antibodies from previously vaccinated or naturally infected individuals. Those satisfying these criteria are used for in-frame fusion with the retargeting component of the final fusion protein. Fusion is mediated through the amplification of the retargeting component using specific primers containing recognition site for restriction endonuclease BamHI. Orientation of the retargeting component must be checked so that the C-terminus of retargeting component is fused to N-terminus of mutagenised MeaHsv thus replacing the original 58 N-terminal amino acids of MeaH. In such construction the natural hinge of the MeaH molecule (see Description) can be used to position the two parts of the fusion protein. Complete fusion proteins undergo the same set of investigations as mutagenised MeaH variants as far as the binding activities and antibody reactivities are concerned.

Example 3

Identification of Proteins Binding to the HIV 1 Envelope (env) Protein for Retargeting Purposes
 a) Screening human expression cDNA library with biotinylated recombinant env
 b) Confirmation of binding in Western blot
 c) Identification of selected cDNA clones by sequencing a) Screening human expression cDNA library with biotinylated recombinant env Biotinylation: Recombinant HIV1 gp120 has been dissolved in phosphate buffered saline (PBS) at 0.5 µg/µl and biotinylated using biotinylation kit (Boehringer, Cat. No1418 165) according to manufacturer's instruction. Briefly, the column was fixed and 5 ml of blocking solution added, then washed with 6×5 ml PBS.
 env: Dissolved in 500 µl PBS
 475 µl taken for labeling
 Add 17.5 µl PBS and 7.5 µl 20 mg/ml biotin-7-NHS in DMSO while stirring
 Place in a tube
 Incubate 2 hrs/rt/rotating wheel
 Remove stopper and cap from prepared column
 Add 500 µl PBS to adjust volume to 1 ml, let flow through
 Add another 1.5 ml PBS, let flow through
 Add 3.5 ml PBS and collect 10 drops (approximately 0.5 ml)
 Protein expected in first 4 tubes—run 7.5 µl on the gel
 After protein assay selected fractions were pooled Screening human expression cDNA library
 cDNA library was prepared by cloning cDNA from human brain into expression vector. The library was grown on agar plates at high density and transferred to nylon filters and lysed and fixed using standard techniques.

Filter Screening:
1) 20 minute incubation in 200 ml absolute ethanol.
2) 1 wash for 5 minutes in 1 litre PBS-T-T (PBS-Tween20).
3) 2 rinses each in 1 litre PBS and a 3rd 5 minute wash in 1 litre of PBS.
4) 45 minute wash in 3% Marvel-PBS.
5) 1 hour incubation in biotinylated env/3% Marvel-PBS
6) 1 wash for 5 minutes in 1 litre PBS-T-T.
7) 2 rinses each in 1 litre PBS and a 3rd 5 minute wash in 1 litre of PBS.
8) 20 ml 1×PBS 3% Marvel
9) 40 minute incubation in 1 in 5000 dilution of streptavidin-horse radish peroxidase (HRP) in 3% Marvel-PBS. 30 µl streptavidin-HRP in 150 ml 3% Marvel-PBS.
10) 2 washes for 5 minutes each in 1 litre PBS-T-T.
11) 2 washes for 5 minutes each in 1 litre PBS.
12) Develop using ECL reagents (Amersham).

b) Confirmation of binding in Western blot (FIG. 2)
 11 positive colonies identified were grown from master plates in liquid overnight cultures.
   Extracts prepared from 20 ml of induced cultures of clones 1-11 using 4× lysis buffer.
   After 3 hr induction cells spun at 4000 rpm for 15'.
   Pellet resuspended in 600 µl water.

52 μl of 1 M DTT and 220 μl 4× lysis buffer (0.2×PBS, 8% SDS) added
Incubation at 37° C. occasional Vortex
Because of cloudy appearance volume raised to 24 ml
Centrifuged 4000 rpm/15'. Pellet discarded 2×12 ml spun in Centriprep10 at 4000 rpm/40'/25° C.
Retentates combined, diluted with 0.5×PBS to 12 ml and spun again under identical conditions
Filtrate discarded and retentates spun again 10'. Final volume around 0.5 ml. 4.5 μl run on the gel and binding confirmed on Western blot with biotinylated env.

Clones 1, 2, 3, 6 and 8: plasmid minipreps prepared from 4 ml overnight cultures, 200-500 ng per sequencing reaction.

Reaction mix Forward (for 6) 24 μl seq. Buffer
  24 μl terminator ready mix
  1.92 μl 1:10 Forward primer (10 pMol/μl)
  8.32 μl of the mix to tubes 1-5

Reaction mix Reverse (for 6) 24 μl seq. Buffer
  24 μl terminator ready mix
  1.92 μl 1:10 Reverse primer (10 pMol/μl)
  8.32 μl of the mix to tubes 6-10

Overlaid with 40 μl oil. Amplification in 96 well plate:
25 cycles: 96° C./30"
  50° C./15"
  60° C./4'
  4° C./hold Spin the tubes. Prepare 1.5 ml tubes containing 2 μl 3 M sodium acetate (pH 4.6-5.2) and 50 μl 95% EtOH. Transfer 20 μl into the tubes. Vortex and place on ice for at least 15 mins. Spin in microcentrifuge for 15-30 mins. Discard supernatant. Rinse with 250 μl 70% Ethanol. Air dry the pellet. Resuspend in 4 μl of 50 mM EDTA (7.4-8.0) and 200 μl deionized formamide. Denature and load.

Results: Clone 1: The nucleotide sequence determined for this HIV-1 env-binding protein corresponds to that of *Homo sapiens* creatine kinase B (GenBank Accession X15334).
  Clone 2: The nucleotide sequence determined for this HIV-1 env-binding protein corresponds to an unknown human protein. The sequence reads as shown in the Description of the Invention. There were two recent entries into GenBank (both in 2000) which contain almost identical sequences: Accession AK026796 and AK000685. Both were submitted after the submission of the original patent application.
  Clone 3: The nucleotide sequence determined for this HIV-1 env-binding protein corresponds to *Homo sapiens* ribosomal protein L8 (RPL8; GenBank Accession NM000973).
  Clone 6: The nucleotide sequence determined for this HIV-1 env-binding protein corresponds to an unknown human protein. Partial sequence reads:

There was a recent submission into Genbank (Sep. 29, 2000) from the Japanese NEDO human cDNA sequencing project (Accession AK023367) containing a virtually identical sequence.
  Clone 8: The nucleotide sequence determined for this HIV-1 env-binding protein is practically identical to that of clone 1, for B subunit of creatine kinase *Homo sapiens*, brain.

Example 4

Chemical Fragmentation of Apolipoprotein B Purified from Human Plasma (Europa Bioproducts Ltd)

Chemical fragmentation has been carried out using a well-known method of protein engineering. Four chemical treatments were chosen based on computer prediction for number of cuts in apolipoprotein B (ApoB) molecule.

Formic acid: Expected: 6 cuts. Treatment of 100 μg of ApoB with 70% formic acid in 7 M guanidinium-HCl for 24 and 48 hrs at 37° C.

Hydroxylamine: Expected: 17 cuts. 100 μg of ApoB has been cleaved in
  2 M hydroxylamine
  2 M guanidine-HCl
  0.2 M $K_2CO_3$ pH 9.0
  for 4 hrs at 45° C. Reaction was terminated by adding concentrated formic acid to pH 2-3 and desalted on Sephadex G-25. Peptides larger than 2500 (m.w.) appear in the void volume.

NTCB (2-nitro-5-thiocyanobenzoate):
  Expected: 25 cuts. 100 μg of ApoB dissolved in 6 M guanidine-HCl 0.2 M tris-acetate buffer pH 8.0
  Dithiothreitol (DTT) added to 10 mM to reduce disulfides. Incubation 1-2 hrs at 37° C. NCTB added in 5-fold excess over total thiol. Incubation for 15 minutes at 37° C. Acidified to pH 4 or less, cooled to 4° C.

Recombinant envelope protein E1 of the Hepatitis C virus (Europa Bioproducts Ltd) has been biotinylated as described for HIV env protein in Example 3 and bound to streptavidin coated paramagnetic particles (Promega) and washed with PBS. Chemically treated preparations of ApoB were diluted in PBS and fragments captured on particles with immobilised E1. Captured fragments were analysed by SDS-PAGE.

Example 5

Binding and Antigenic Properties of Mutated MeaH

Selected mutant constructs of MeaH were subcloned into pSPUTK in Vitro Translation Vector (Stratagene) and expressed in vitro according to manufacturer's instruction.

```
5'GGAGAAGGTCTCTGAAGGAGAAAAGCAAAGAAGCTCTTTTG     (SEQ ID NO:15)
GCCTCACAAAAGCCATTTAAATTTATAGCAAGGGAGGAACAG
AAGCGAGCAGCCCGGGAAAAGCAGCTGAGAGACTTTCTTAAG
TATAAAAAGAAAACAAATCGATTTAAAGCCAGACCCATTCCT
CGATCTACTTATGGTTCAACTACCAATGACAAGTTAAAAGAAG
AAGAGCTCTATCGAAACCTTAGGACACAGCTGAGAGCCCAGG
AGCATTTACAGAACTCATCTCCTCTGCCTTGTAGGTCAGCTTG
CGGATGCAGGAACCCCAGGTGTCCTGAACAGGCTGTAAAGTT
GAAGTGTAAACACAAGGTTAGGTGCCCACTCCTGATTTTGAGG
ACCTTCTGAGAGATACCAGAACCCTCTCAAACACAAGTCTTCA
AAACTCTAACAGG3'
```

The products were investigated for their binding to CD46 ectodomain or CD46 expressing cells as described [Devaux et al, Journal of General Virology 77, 1477-1481 (1996)].

Hemagglutination assay using Edmonston MV and preincubation of erythrocytes with pSPUTK/MeaH products is as described by Norrby and Gollmar [Infect. Immunity 11, 231-239 (1975)].

Presence of antiMeaH antibodies in anonymous plasma/serum samples is determined using a commercial assay. Reactivity of these samples towards the ectodomain of normal and mutated MeaH, as well as fusion proteins with appropriate component 2, is determined after coating wells of Maxisorb 96 well plates with investigated in vitro translated proteins (pSPUTK). Plates are blocked with PBS-Marvel, incubated with 1:10 diluted plasma/serum samples, washed repeatedly with PBS/Tween 20, incubated with protein L-HRP (horse radish peroxidase) conjugate and washed again. Reactivity is revealed after incubation with HRP substrate (TSB). The development is stopped by adding sulphuric acid and the result obtained using ELISA reader.

What is claimed is:

1. A recombinant bifunctional fusion protein which comprises a first component which is a measles virus protein modified so that it does not bind to a CD46 receptor nor cause hemadsorption nor hemagglutination, but is recognized by anti-measles antibodies, wherein the first component is the ectodomain of measles virus hemagglutinin protein (MeaH) which has been modified by removal of between 58 to 100 N-terminal amino acids; by mutagenesis of amino acids 243, 451 and 481; and by the introduction of deletions in the amino acid regions 244-250 and 450-505; and a second component fused to the first component that binds a surface protein of human immunodeficiency virus (HIV).

2. The recombinant fusion protein of claim 1 wherein the second component is fused to the N-terminus of the first component.

3. The recombinant fusion protein of claim 1 wherein the second component is a protein of human origin.

4. The recombinant fusion protein of claim 1 wherein the second component is human creatine kinase B.

5. The recombinant fusion protein of claim 1, wherein the second component is a part of human creatine kinase B that binds HIV envelope protein gp120.

6. The recombinant fusion protein of claim 4 wherein the human creatine kinase B is a variant of human creatine kinase differing therefrom by not more than 5% of amino acid positions and that binds HIV envelope protein gp120.

7. The recombinant fusion protein of claim 1 wherein the second component is a human single chain antibody (scFv) that binds HIV.

8. An isolated nucleic acid sequence encoding the recombinant fusion protein of claim 1.

9. A composition comprising the recombinant fusion protein of claim 1 in a pharmaceutically acceptable carrier.

10. A composition comprising the nucleic acid of claim 8 in a pharmaceutically acceptable carrier.

* * * * *